(12) United States Patent
Nirvanashetty et al.

(10) Patent No.: US 12,419,930 B2
(45) Date of Patent: Sep. 23, 2025

(54) BIOAVAILABLE TURMERIC COMPOSITION AND PROCESS FOR PREPARATION THEREOF

(71) Applicant: OLENE LIFE SCIENCES PRIVATE LIMITED, Chennai (IN)

(72) Inventors: Somashekara Nirvanashetty, Chennai (IN); Sanjib Kumar Panda, Chennai (IN); Vivek Anand Parachur, Chennai (IN)

(73) Assignee: OLENE LIFE SCIENCES PRIVATE LIMITED, Chennai (IN)

( * ) Notice: Subject to any disclaimer, the term of this patent is extended or adjusted under 35 U.S.C. 154(b) by 839 days.

(21) Appl. No.: 17/547,734

(22) Filed: Dec. 10, 2021

(65) Prior Publication Data

US 2022/0168378 A1 Jun. 2, 2022

Related U.S. Application Data

(63) Continuation-in-part of application No. PCT/IN2020/050519, filed on Jun. 11, 2020.

(30) Foreign Application Priority Data

Jun. 11, 2019 (IN) .............................. 201941023055

(51) Int. Cl.
*A61K 36/9066* (2006.01)
*A61K 31/12* (2006.01)

(52) U.S. Cl.
CPC .......... *A61K 36/9066* (2013.01); *A61K 31/12* (2013.01)

(58) Field of Classification Search
None
See application file for complete search history.

(56) References Cited

U.S. PATENT DOCUMENTS

| 6,440,468 B1 | 8/2002 | Quintanilla Almagro et al. |
| 8,895,087 B2 | 11/2014 | Antony |
| 2014/0010903 A1 | 1/2014 | Madhavamenon et al. |

FOREIGN PATENT DOCUMENTS

| WO | 2015/025263 A1 | 2/2015 |

OTHER PUBLICATIONS

Krishnakumar et al., 'Enhanced absorption and pharmacokinetics of fresh turmeric (*Curcuma longa* L) derived curcuminoids in comparison with the standard curcumin from dried rhizomes,' Journal of Functional Foods. 2015, vol. 17, p. 55.
International Search Report from PCT/IN2020/050519; Jul. 2019; 5 pages.
Written Opinion of the International Searching Authority from PCT/IN2020/050519; Sep. 30, 2020; 7 pages.

*Primary Examiner* — Susan Hoffman
(74) *Attorney, Agent, or Firm* — Kramer & Amado, P.C.

(57) ABSTRACT

A turmeric composition having enhanced self-dispersibility and bioavailability includes a solvent free, fresh turmeric rhizome extract and a dried turmeric rhizome extract (standardized to 35-95% total curcuminoids). The turmeric composition may be devoid of externally added excipients/bio-enhancing agents/dispersing agents. A process for preparation of the bioavailable turmeric composition is disclosed herein.

Figure 1:
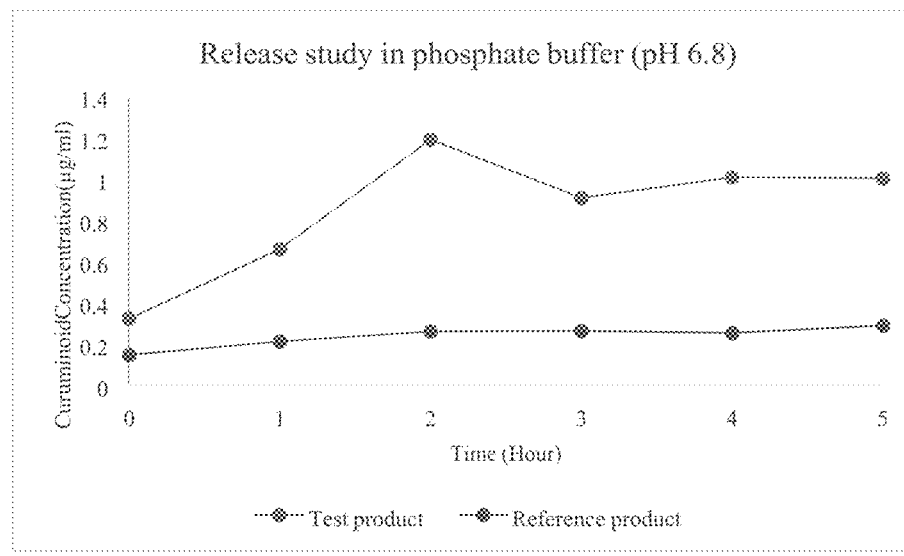

13 Claims, 7 Drawing Sheets a) Test Product b) Reference Product

A = Test Product; B = Reference Product

A = Test Product; B = Reference Product

A = Test Product; B = Reference Product

A = Test Product; B = Reference Product

BIOAVAILABLE TURMERIC COMPOSITION AND PROCESS FOR PREPARATION THEREOF

CROSS-REFERENCE TO RELATED APPLICATIONS

This application is a continuation-in-part of parent International Application No. PCT/IN2020/050519, filed on Jun. 11, 2020, which claims priority to Indian Patent Application No. 201941023055, filed on Jun. 11, 2019. The entire disclosure of each prior application is incorporated by reference herein in its entirety.

TECHNICAL FIELD OF THE INVENTION

The present invention relates to a turmeric composition, free of excipients and external bio-enhancing agents, having enhanced self-dispersibility and bioavailability. The present invention also relates to a process for preparation of said turmeric composition.

BACKGROUND AND PRIOR ART OF THE INVENTION

Natural plant products have been used throughout human history for various purposes. Currently the use of natural products in food and medicine is also increased. This has led to an intense research in to plant extracts and their health benefits. Traditionally known benefits of plants are being analysed and validated for pharmacological benefits. At the same time they are compared against modern pharmaceutical drugs for their efficacy. Many of the natural products have pharmacological or biological activity that can be exploited in pharmaceutical drug discovery and drug design. Medicines derived from plants have played an essential role in the health care of many cultures, both ancient and modern.

One of the well-known plants, extensively used in food and nutraceutical industry is turmeric. Turmeric (*Curcuma longa*) is a member of ginger family (Zingiberaceae). It is a perennial rhizomatous herbaceous plant native to southern Asia, extensively cultivated in all parts of India. Turmeric is extensively used in south Asian cuisine, particularly in India. Turmeric has long history of use for its medicinal properties in traditional remedies, particularly in Ayurveda such as antiinflammatory, anti-oxidant, anti-microbial, anti-arthritic and anti-cancer activities.

Curcuminoids are the most active components of turmeric. They are the primary non-volatile components of turmeric. Curcuminoids are polyphenolic pigments and include curcumin, demethoxycurcumin, and bisdemethoxycurcumin.

Curcumin is a hydrophobic polyphenol derived from the rhizome of the herb *Curcuma longa* has a wide spectrum of biological and pharmacological activities. Curcumin which make up for about 80% of the curcuminoids, is the most studied component of turmeric which is also responsible for giving turmeric its unique yellow colour. Curcumin is known for its antiinflammatory and antioxidant activities; curcumin has also shown activities to reduce oxidative damage related to aging.

Curcuminoids 95% is the most common form of curcuminoids extract composition available in the market. This is a concentrate of 95% curcuminoids, however, the bioavailability of these compositions are very poor.

The established pharmacological safety and efficacy of curcumin makes it a potential compound for treatment and prevention of a wide variety of human diseases, however, curcumin has not yet been considered as a therapeutic agent and the bioavailability of curcumin has been highlighted as a major problem for this.

There are different causes for reduced bioavailability of any agent within the body such as low intrinsic activity, poor absorption, high rate of metabolism, inactivity of metabolic products and/or rapid elimination and clearance from the body. However, the research carried out over past few years on turmeric revealed that poor absorption, rapid metabolism and elimination of curcumin are major reasons that severely decrease its bioavailability.

To improve the bioavailability of curcumin, numerous approaches have been undertaken.

U.S. Pat. No. 6,440,468 disclose a process for preparing a composition for oral administration, the composition containing an apolar extract and a polar extract from *Curcuma longa* rhizome. The process for obtaining the apolar extract comprises: (a) extracting the rhizomes with an organic solvent; (b) filtration and evaporation to dryness of the extract; (c) dissolution of the oleoresin obtained in hot conditions, precipitation while allowing to cool down and filtration of the solid; (d) drying and recrystallizing the solid in order to obtain a product having a purity in curcuminoids higher than 90%. The polar extract comprises: (a) extraction of the rhizomes with water at 50-70° C. and (b) filtration and evaporation of the water. However, US'468 use the solvents for preparation of apolar and polar extract and the percentage yield of obtained curcuminoids using said methods is less (around 8%).

US2014010903, its corresponding 2686/CHE/2012 and research article of Krishnakumar, Dinesh Kumar, Eapen Ninan, et al., titled, 'Enhanced absorption and pharmacokinetics of fresh turmeric (*Curcuma Longa* L) derived curcuminoids in comparison with the standard curcumin from dried rhizomes' published in Journal of Functional Foods. 2015, Vol. 17, p. 55 relates to a curcuminoid composition with enhanced bioavailability derived from fresh turmeric rhizomes and a process for its preparation. However, the process for preparation of composition disclosed and claimed in US'903 is essentially comprises of ultrasonication and enzyme treatment. The enzyme treatment enhances the juice yield, clarity of juice and curcuminoid concentration in the juice. Further ultrasonication after enzyme treatment is effective for enhancing the curcuminoid concentration in the resulting juice and after processing, the percentage yield of obtained juice powder is around 6 to 10% and percentages of curcumin content in juice powder is around 2 to 7%.

WO2015/025263 discloses a curcumin composition for increasing the bioavailability of curcumin, which consists of curcumin mixture and water extract in a ratio of 70:30. The curcumin mixture comprises curcumin dry crystals, volatile oil, fixed oil whereas water extract comprises soluble proteins, dietary fibers and carbohydrates extracted from turmeric. The composition also consists of a natural emulsifier isolated from *Quillaja saponaria* and lecithin.

The prior art process or methods for extraction of curcuminoids uses different organic solvents, lengthy and costly process steps. Moreover, the product thus obtained will have low yield, less curcuminoids content and poor bioavailability. The liquid extract of fresh rhizome will lead to the product with very low levels of curcuminoids and the percentage curcuminoids will be equivalent to dried turmeric rhizome powder. Also, the compositions in the art are generally comprises volatile oil, fixed oil, emulsifiers and external bio-enhancing agents such as PVP and polysorbate which may have safety issues. There is no disclosure of any bioavailable turmeric composition which is devoid of added excipients or solvent or volatile/fixed oil or gum in the art.

Thus, there is still a need exist in the art to provide a turmeric composition comprising higher percentages of curcuminoids, free of oils, any excipients and external bio-enhancing agents, however, achieves improved solubility/dispersibility, thereby providing enhanced bioavailability.

Also in general, if a drug is not soluble in water or has a very low solubility it cannot be absorbed through the cell membranes and thus its absorption will be negligible and consequently its bioavailability will be too low.

OBJECT OF THE INVENTION

In view of the above, the inventors of the present invention have come up with a bioavailable Turmeric composition comprising turmeric extract containing higher amounts of curcuminoids prepared by environmental friendly process of physical methods and co-boiling/homogenization of fresh turmeric rhizome extract and dried turmeric rhizome extract (standardized to 35-95% total curcuminoids) at higher temperature, without use of any excipients and external bio-enhancing agents, still achieving enhanced self-dispersibility and bioavailability. The final composition comprises 100% turmeric derived composition.

SUMMARY OF THE INVENTION

In accordance with the above objective, the present invention discloses a 100% pure turmeric composition having higher percentage of curcuminoids with enhanced self-dispersibility and bioavailability.

In a preferred aspect, the present invention discloses a highly bioavailable and self-dispersible turmeric composition comprising a fresh turmeric rhizome extract and dried turmeric rhizome extract standardized to 35-95% total curcuminoids, in a ratio ranges from 0.5:50 to 50:0.5 v/w.

In another aspect, the present invention discloses a turmeric composition that is free of any externally added excipients, bio-enhancing agents, emulsifiers, dispersing agents, solvents, fixed oils, volatile oils or gums.

In another preferred aspect, the present invention discloses a turmeric composition comprising curcuminoids that contains Curcumin, Demethoxycurcumin (DMC) and Bis-demethoxycurcumin (BDMC) in their native profile.

In yet another preferred aspect, the present invention discloses a process for preparation of said turmeric composition comprising homogenizing/wet milling/colloidal milling of fresh turmeric rhizome extract and dried turmeric rhizome extract standardized to 35-95% total curcuminoids together at higher temperature followed by drying and powdering to get the free-flowing powder of self-dispersible turmeric composition.

In yet another aspect, the present turmeric composition enhances the bioavailability of Curcumin, Demethoxycurcumin (DMC), Bismethoxycurcumin (BDMC) and Tetrahydrocurcumin (THC), an active metabolite of Curcumin.

In yet another aspect, the present turmeric composition enhances the bioavailability of DMC, BDMC and THC significantly higher than unformulated standard curcuminoids (C-95) extract.

Various embodiments disclosed herein relate to a bioavailable and self-dispersible turmeric composition, including a turmeric extract, containing:

5% to 50%, 5% to 40%, 5% to 30%, 10% to 30%, or 15% to 25% by weight of a solvent free extract of fresh turmeric rhizomes comprising <4% hydrophobic contents by dry weight, and 20% to 95%, 30% to 95%, 40% to 95%, 50% to 95%, 60% to 95%, 70% to 95%, 70% to 90%, or 75% to 85% by weight of a dried turmeric rhizome extract containing 35% to 95% total curcuminoids by weight, based on the combined weight of the fresh turmeric rhizome extract and the dried turmeric rhizome extract by dry weight. The turmeric extract may be present in an amount effective to treat an inflammatory disease, a cognitive disease, an eye disease, a skin disease, stress, or a combination thereof. The bioavailable and self-dispersible turmeric composition may be free of externally added excipients, bio-enhancing agents, emulsifiers, dispersing agents, solvents, fixed oils, volatile oils, and gums.

In various embodiments, the turmeric composition includes:
20% to 85% by weight of total curcuminoids in a self-dispersible form,
0.25% to <4% of proteins; and
0.25% to <49% of carbohydrates.

In various embodiments, the turmeric composition includes 20% to 85% by weight of total curcuminoids in a self-dispersible form, and the total curcuminoids include curcumin in an amount of 15% to 74%, desmethoxycurcumin (DMC) in an amount of 10% to 30%, and bisdemethoxycurcumin (BDMC) in an amount of 3% to 20%.

Various embodiments disclosed herein relate to a bioavailable and self-dispersible turmeric composition, comprising:
a turmeric extract, comprising:
5% to 80%, or 5% to 30%, by weight of a solvent free extract of fresh turmeric rhizomes comprising <4% hydrophobic contents by dry weight, and
20% to 95%, or 70% to 95%, by weight of a dried turmeric rhizome extract containing 35% to 95% total curcuminoids by weight,
based on the combined weight of the fresh turmeric rhizome extract and the dried turmeric rhizome extract,
wherein the turmeric extract is present in an amount effective to treat an inflammatory disease, a cognitive disease, an eye disease, a skin disease, stress, or a combination thereof.

BRIEF DESCRIPTION OF FIGURE(S)

FIG. 1: Release profile of Turmeric Composition 1 of Example 1

Figure 2A:
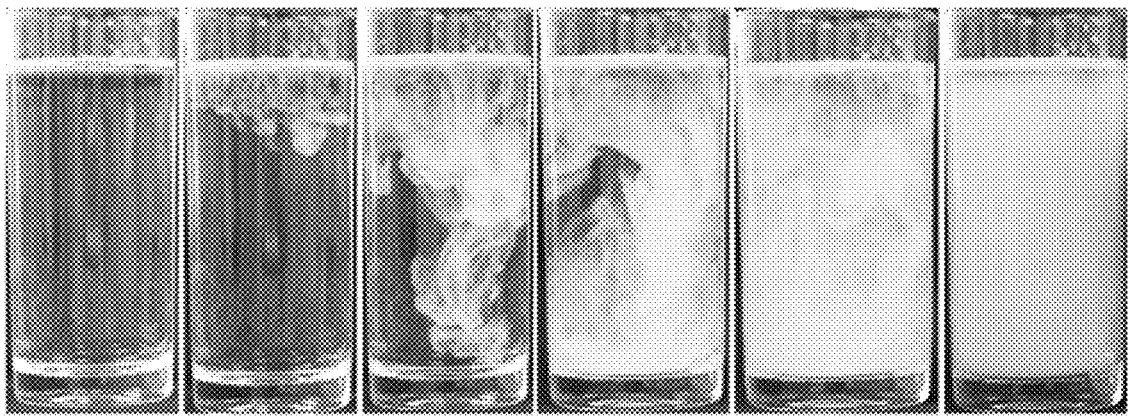
Figure 2B:
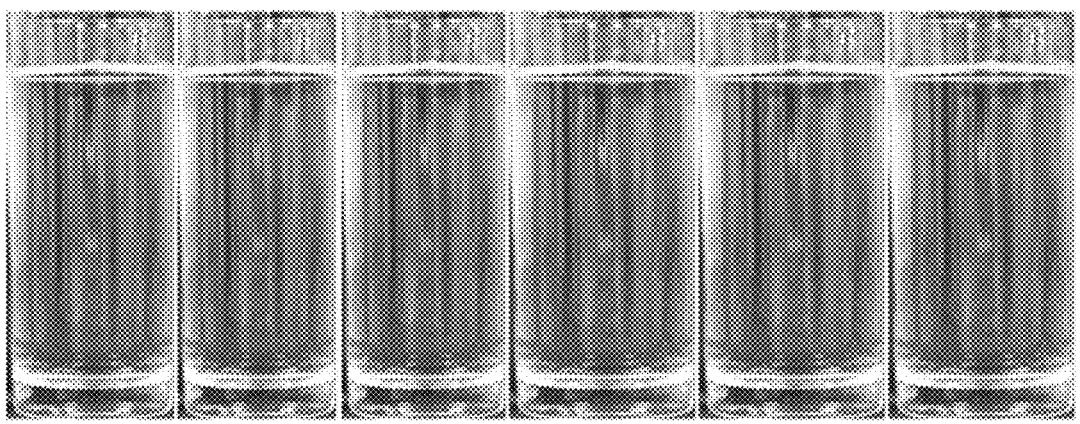

FIGS. 2A and 2B: Dispersion FIG. 2A shows a dispersion study of Turmeric Composition 1. FIG. 2B shows a dispersion study of a standard curcumin extract (95% total curcuminoids).

Figure 3:
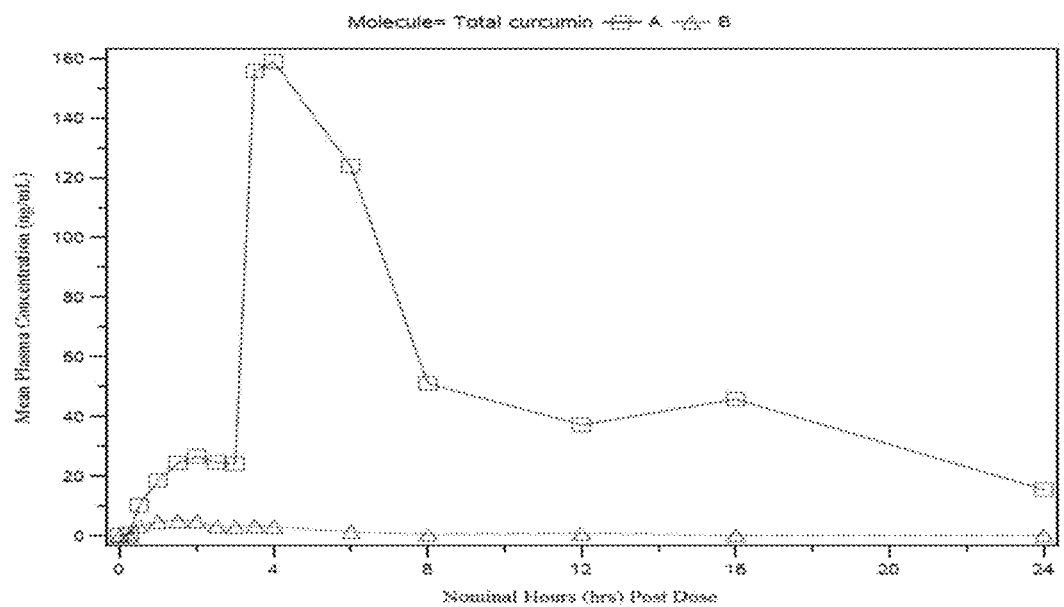

FIG. 3: Mean plasma Total Curcumin Concentration Vs. Time graph of Turmeric Composition 1

Figure 4:
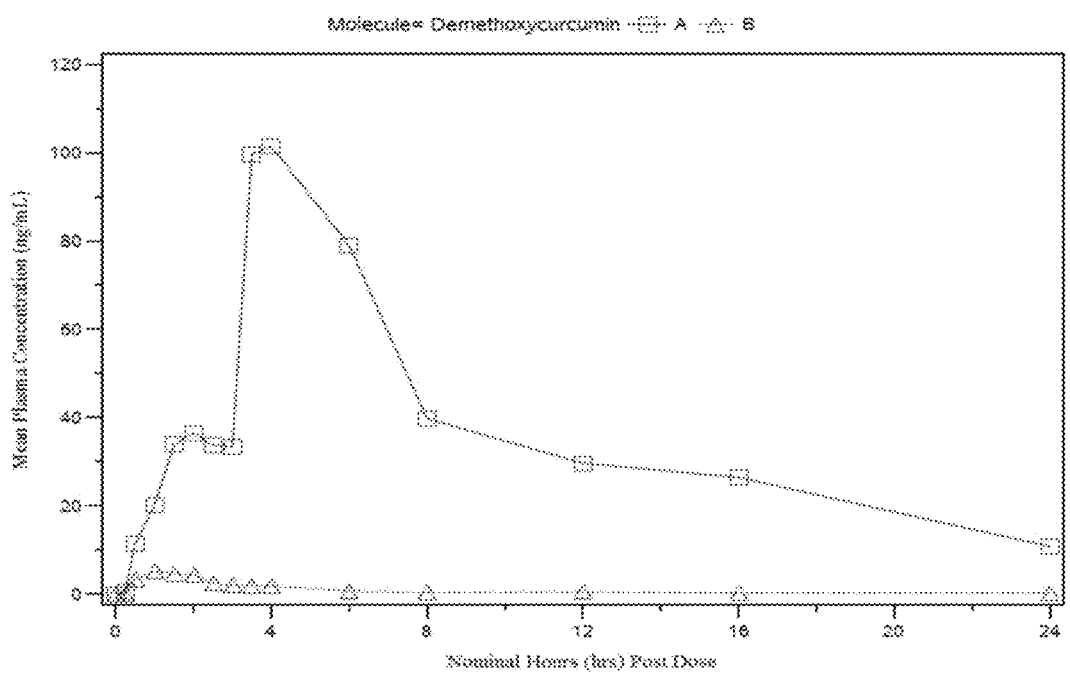

FIG. 4: Mean plasma Demethoxycurcumin (DMC) Concentration Vs. Time graph of Turmeric Composition 1

Figure 5:
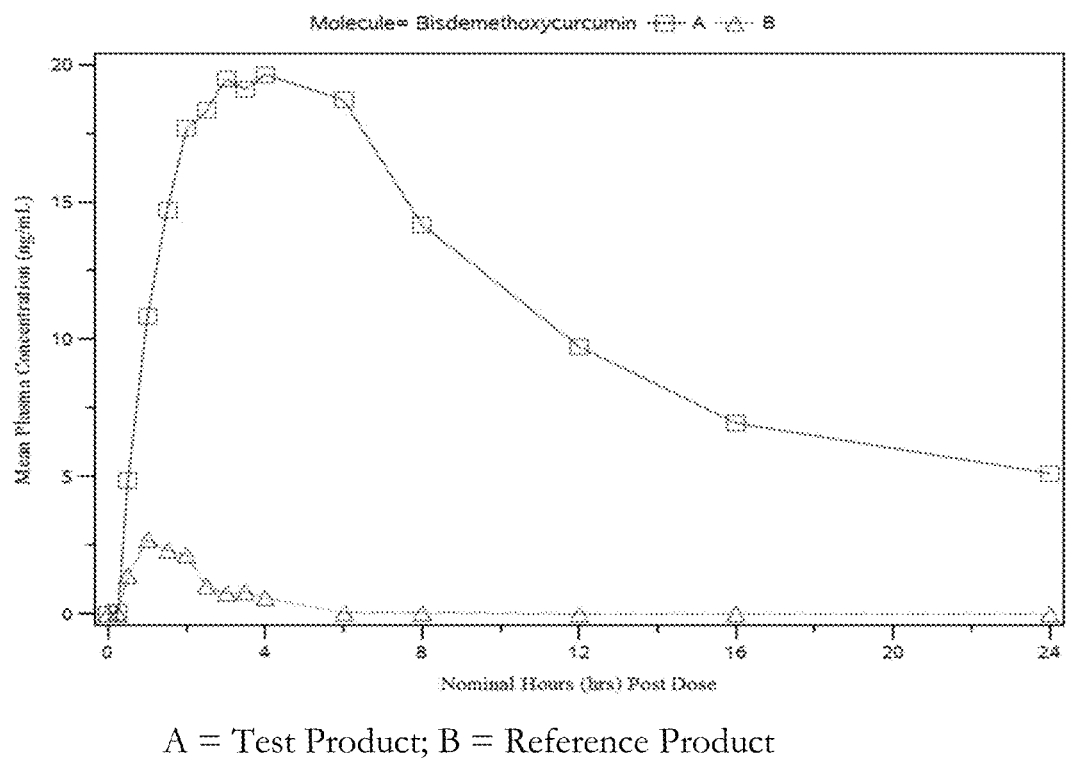

FIG. 5: Mean plasma Bismethoxycurcumin (BDMC) Concentration Vs. Time graph of Turmeric Composition 1

Figure 6:
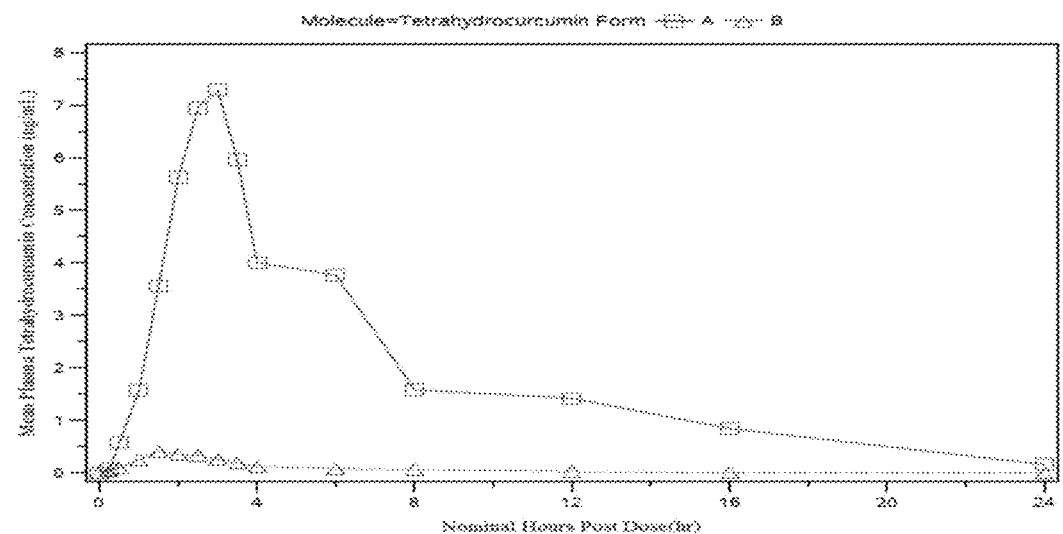

FIG. 6: Mean plasma Tetrahydrocurcumin (THC) Concentration Vs. Time graph of Turmeric Composition 1

Figure 7:
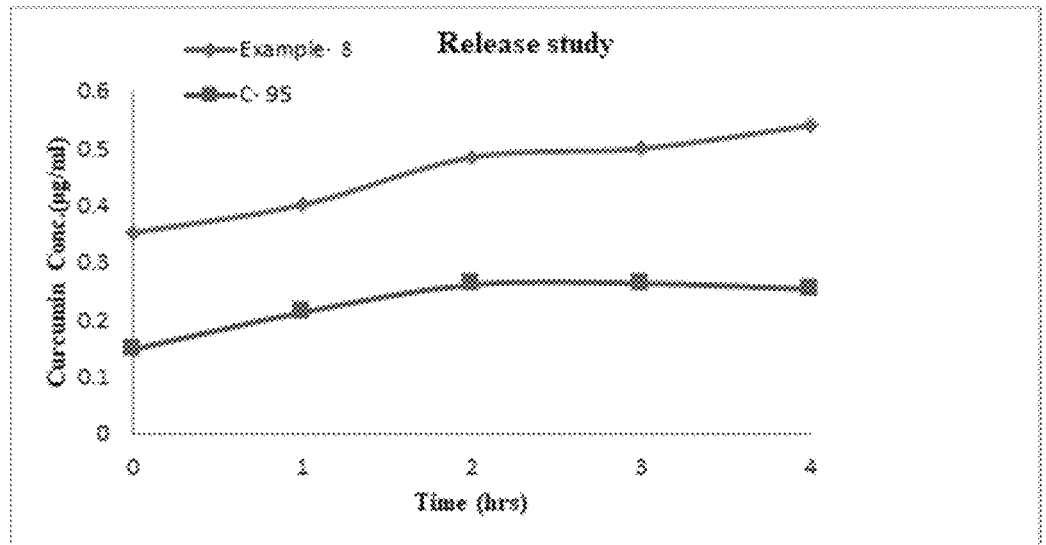

FIG. 7: Release profile of Turmeric Composition 2 of Example 8

Figure 8:
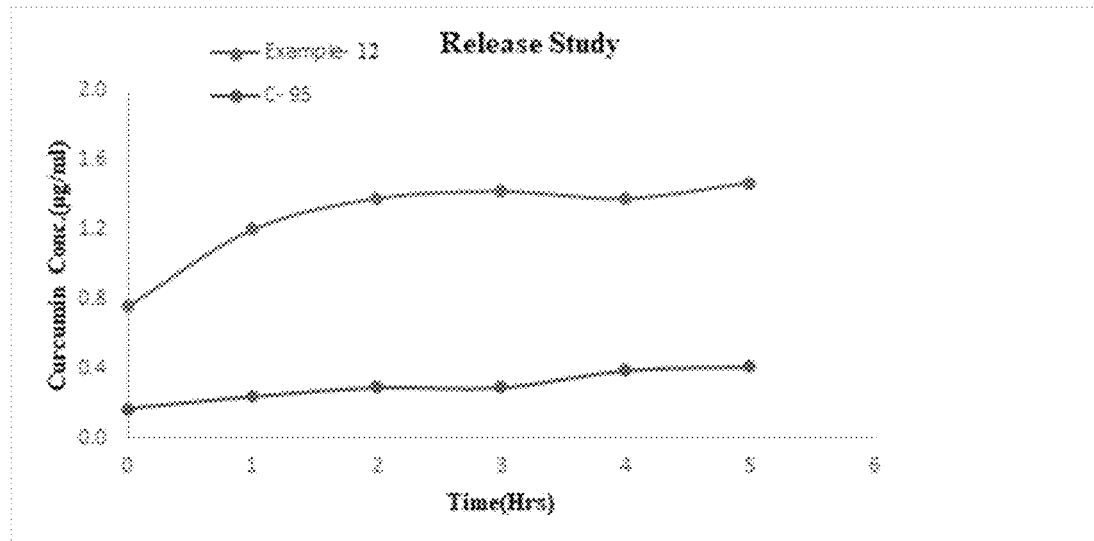

FIG. 8: Release profile of Turmeric Composition 3 of Example 12

Figure 9:
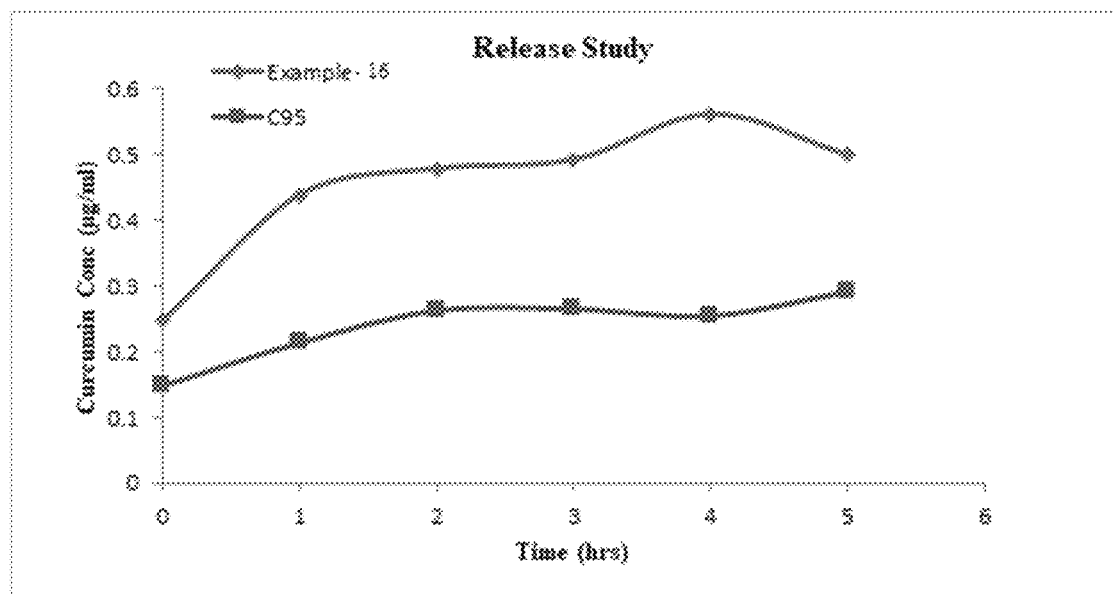

FIG. 9: Release profile of Turmeric Composition 4 of Example 16

Figure 10:
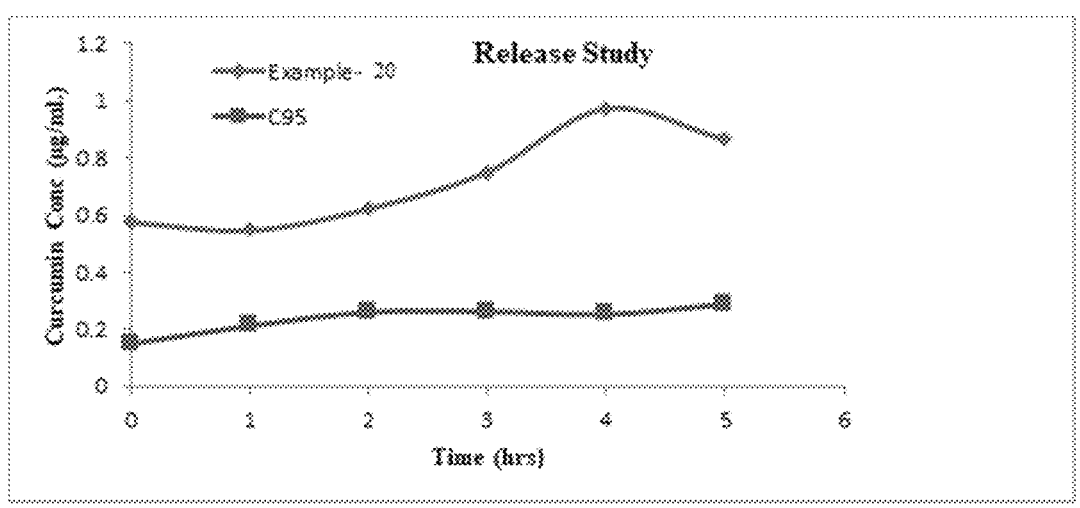

FIG. 10: Release profile of Turmeric Composition 5 of Example 20

Figure 11:
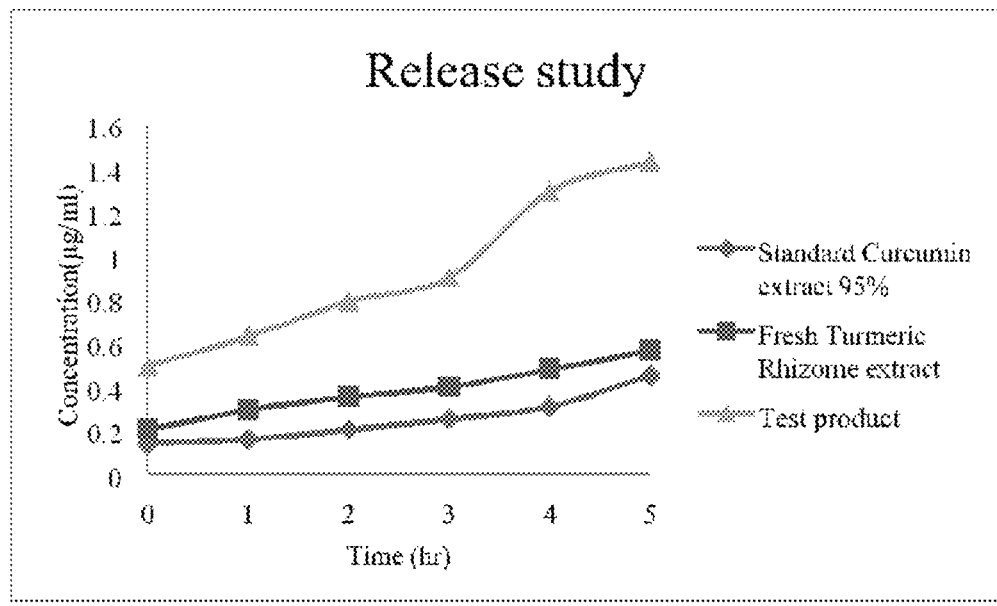

FIG. 11: Release profile of Turmeric Composition 1 of Example 1 vis-à-vis standard curcumin extract (95% total curcuminoids) and fresh turmeric rhizome extract FIG. 12: Release profile of Turmeric Composition 1 of Example 1 vs. Marketed Product

DETAILED DESCRIPTION OF THE INVENTION

The invention will now be described in detail in connection with certain preferred and optional embodiments, so that various aspects thereof may be more fully understood and appreciated.

Source and Geographical Origin of the Biological Material Used in the Invention:

*Curcuma longa* (Turmeric)

Geographical Origin: Native to the Indian subcontinent and Southeast Asia Source: The turmeric rhizome was procured from local vendor (farmer) of Erode District, Tamil Nadu, India.

The term 'dried turmeric rhizome extract' refers herein is the dried turmeric rhizome extract which is standardized to 30-95% total curcuminoids and includes partially purified Oleoresin extract and extract with 95% Total Curcuminoids.

The term 'Self-dispersible' refers herein to spontaneous dispersion of a product into aqueous phase forming uniform suspension without any external force applied to make it disperse.

The term "fresh," as applied to a plant or plant part, may in various embodiments refer to a freshly harvested plant part, or to a plant part obtained from a freshly harvested plant. The term "fresh," as applied to a plant or plant part, may in various embodiments refer to a plant or plant part having a water content of 60% to 98%, 65% to 98%, 65% to 97%, 70% to 97%, 75% to 97%, 78% to 96%, 80% to 96%, 85% to 95%, or 85% to 93% by weight. The term "fresh," as applied to a plant or plant part, may in various embodiments refer to a plant or plant part having a water content of >60% by weight. In various embodiments, a fresh plant or plant part is not subjected to further post-harvest processing such as drying, milling, and/or solvent extraction.

The term "native profile of curcuminoids" may in various embodiments refer to a percentage content of curcumin, demethoxycurcumin, and bisdemethoxycurcumin in a freshly harvested turmeric rhizome/dried turmeric rhizome.

The fresh extract of a plant part may be considered as a liquid extract obtained by extrusion of a fresh plant part containing >60% water. The solid content in the liquid extract of a fresh plant part may be <40%, <30%, <25%, 3% to 20%, 5% to 18%, or 5% to 13%. When a liquid extract of a fresh plant part is mixed with a dried turmeric extract, the ratio of liquid fresh plant part extract to dried turmeric extract is measured in "v/w." In various embodiments, the liquid extract of the fresh plant part may be dried to obtain a solid, and this solid may be combined with a dried turmeric extract. For example, 77 mL of a liquid extract of a fresh plant part with a solids content of 13% may be dried to produce 10 g of a solid extract of a fresh plant part. Similarly, 200 mL of a liquid extract of a fresh plant part with a solids content of 5% may be dried to produce 10 g of a solid extract of a fresh plant part. In general, when amounts of the content of an extract of a fresh plant part extract are described in terms of a dry basis or a dry weight, this means either:

Solids content of a liquid extract; or

Solid mass obtained after drying a liquid extract.

The present invention discloses a 100% pure turmeric composition having higher percentage of curcuminoids with enhanced self-dispersibility and bioavailability.

In a preferred embodiment, the present invention discloses a highly bioavailable and self-dispersible turmeric composition comprising a fresh turmeric rhizome extract and dried turmeric rhizome extract (standardized to 35-95% total curcuminoids), in a ratio ranges from 0.5:50 to 50:0.5 v/w. The composition may be devoid of any externally added excipients, bio-enhancing agents, emulsifiers, dispersing agents, solvents, fixed oils, volatile oils or gums.

In another embodiment, the turmeric composition of the present invention comprises 20 to 85% of total curcuminoids content in self-dispersible form, 0.25 to <4% of proteins content and 0.25 to <49% of carbohydrates content.

In another embodiment, the present invention discloses a method for enhancing the bioavailability of curcuminoids using solvent free fresh turmeric rhizome extract; wherein said method comprising extraction of solvent free fresh turmeric rhizome extract, homogenizing/wet milling/colloidal milling of fresh turmeric rhizome extract and dried turmeric rhizome extract standardized to 35-95% total curcuminoids together at higher temperature followed by drying and powdering to get the free-flowing powder of self-dispersible turmeric composition.

In a preferred embodiment, the present invention discloses a cost effective, ecofriendly process for preparation of turmeric composition comprising the steps of;

a) slicing the fresh turmeric rhizome and washing with water followed by squeezing to separate the liquid extract and filtering the extract;

b) heating the extract of step (a) up to 60° C. with continuous stirring for 30 minutes;

c) adding dried turmeric rhizome extract (standardized to 35-95% total curcuminoids) to the extract of step (b) in the ratio ranging from 0.5:50 to 50:0.5;

d) continuously homogenizing the mixture of step (c) for 30 to 60 minutes between 25° C. to 60° C. at 1400 RPM to obtain slurry; and e) vacuum drying the slurry of step (d) at 60° C. to 85° C. for 8 hours followed by milling the flakes to obtain free flowing powder of self-dispersible turmeric composition.

In various embodiments, the liquid extract obtained from the fresh turmeric rhizome contains <2% curcuminoids, on a dry basis.

Accordingly, the process for preparation of present turmeric composition comprising the steps of;

a) slicing the fresh turmeric rhizome and washing with RO water followed by squeezing using low screw extruder with 0.5 mm to 1 mm mesh to separate the liquid extract and filtering the extract;

b) heating the extract obtained in step (a) up to 60° C. with continuous stirring for 30 minutes using a homogenizer;

c) slowly adding dried turmeric rhizome extract standardized to 35-95% total curcuminoids to the extract of step (b) in the ratio ranging from 0.5:50 to 50:0.5; with continuous homogenizing for 30 to 60 minutes at 1400 RPM between 25° C. to 60° C. to obtain viscous slurry;

d) vacuum drying the slurry of step (c) at 60° C. to 85° C., 650 mmHg vacuum for 8 hours by Rotary Vacuum Dryer (RVD) and e) milling the flakes of step (d) to obtain free flowing powder (particle size >120 mesh) of self-dispersible turmeric composition.

In the present process, fresh turmeric rhizome was washed with the RO water and squeezed using low speed screw extruder with 0.5 mm to 1 mm mesh to separate the liquid extract and filtered the extract. The extract obtained was heated up to 60° C. with continuous stirring for 30 minutes using a homogenizer. Dried turmeric rhizome extract standardized to 35-95% total curcuminoids was slowly added to the fresh turmeric rhizome extract and continuously homogenized for 30 to 60 minutes at 1400 RPM between 25° C. to 60° C. to obtain viscous slurry. The slurry was vacuum dried at 60° C. to 85° C., 650 mmHg vacuum for 8 hours by Rotary Vacuum Dryer (RVD) and milled using comminuting mill to get free flowing powder (particle size >120 mesh). This final free flowing powder contains >20% total curcuminoids and is highly self-dispersible and bioavailable.

The percentage yield of fresh liquid extract from fresh turmeric rhizome is ranging from 50 to 80% with a solid content ranging from 5 to 13%.

In another embodiment, the fresh turmeric rhizome extract obtained by using low speed screw extruder with 0.5 mm to 1 mm mesh is a solvent free extract comprising <4% hydrophobic contents and acts as dispersing agent.

In another embodiment, the fresh turmeric rhizome extract can be dried into powder for storage which can be reconstituted with water and used.

The ratio of fresh turmeric rhizome extract to dried turmeric rhizome extract standardized to 35-95% total curcuminoids is 0.5:50 to 50:0.5 v/w.

In another embodiment, the dried turmeric rhizome extract standardized to 35-95% total curcuminoids is extracted from dried turmeric rhizome using solvents such as ethanol, ethyl acetate, methanol, acetone and hexane.

The homogenization or wet milling or colloidal milling of fresh turmeric rhizome liquid extract and dried turmeric rhizome extract standardized to 35-95% total curcuminoids at higher temperature enhances the self-dispersion and bioavailability of curcuminoids.

The bioavailable turmeric composition of present invention comprises higher amount of curcuminoids (20 to 85%) and are amorphous in nature.

In another preferred embodiment, the present turmeric composition comprises curcuminoids that contains curcumin in an amount ranges from 15 to 74%; Demethoxycurcumin (DMC) in an amount ranges from 10 to 30%, and Bisdemethoxycurcumin (BDMC) in an amount ranges from 3 to 20%. These ranges are similar to fresh turmeric extract/dried turmeric root powder.

In another embodiment, the present turmeric composition enhances the bioavailability of Curcumin, Demethoxycurcumin (DMC), Bismethoxycurcumin (BDMC) and Tetrahydrocurcumin (THC), an active metabolite of Curcumin.

In another embodiment, the present turmeric composition enhances the bioavailability of DMC, BDMC and THC significantly higher than unformulated standard curcuminoids (C-95) extract.

In another embodiment, the present turmeric composition delivers higher levels of DMC, BDMC and THC into the blood compared to unformulated standard curcuminoids.

In another embodiment, the present invention discloses the release profile of turmeric composition; wherein the results exhibit the increased solubility and sustained release for present composition compared to unformulated standard curcuminoids (having 95% total curcuminoids, C-95). The same is depicted in FIG. 1 and FIGS. 7 to 10.

In another embodiment, the present invention discloses the comparative self-dispersion study between the present turmeric composition and unformulated standard curcuminoids (having 95% total curcuminoids, C-95); wherein the result show that present composition exhibits enhanced self-dispersion compared to the unformulated standard curcuminoids which floats on top of the water. The dispersion result is given in FIG. 2.

In another embodiment, the present invention discloses the bioavailability and pharmacokinetics profile of present turmeric composition; wherein the results exhibit that the present turmeric composition was found to be superior to unformulated standard curcuminoids (standardized to 95% total curcuminoids) in enhancing the bioavailability of total Curcumin, Demethoxycurcumin (DMC), Bisdemethoxycurcumin (BDMC) and Tetrahydrocurcumin (THC). The same is depicted in FIG. 3 to FIG. 6.

In another embodiment, the present invention discloses synergy of the present turmeric composition; wherein the results show that present composition exhibits increased release profile compared to 'unformulated standard curcuminoids (having 95% total curcuminoids, C-95)' and 'fresh turmeric rhizome extract powder'. The same is depicted in FIG. 11.

Figure 12:
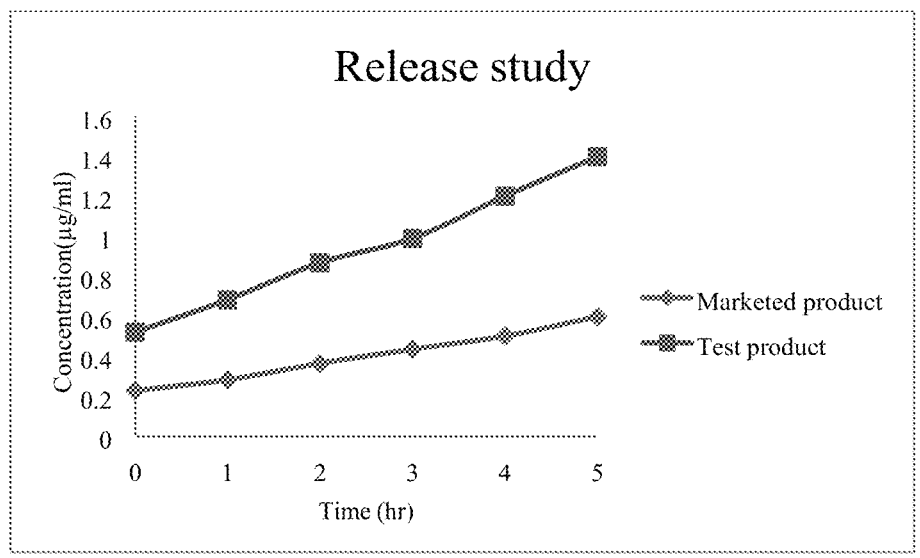

In another embodiment, the present invention discloses efficacy of the present turmeric composition; wherein the result shows that present composition exhibits increased release profile compared to 'marketed product' (composition comprising fresh rhizome juice powder as disclosed in Patent No. US2014010903). The same is depicted in FIG. 12.

In another embodiment, the turmeric composition of the present invention may be devoid of any externally added excipients, dispersing agents, bio-enhancing agents, emulsifiers, solvents, fixed oils, volatile oils or gums and having enhanced self-dispersibility and bioavailability.

The present bioavailable turmeric composition is in the form of powder which can be formulated into various dosage forms such as tablets, capsules, pills, solutions, pastes, lozenges, ready to drink beverages (RTDs), beverages and the like.

In another embodiment, the present invention discloses the use of bioavailable turmeric composition in the treatment of inflammatory diseases, cognitive diseases, eye diseases, skin diseases, stress and the like.

In another embodiment, the present invention discloses a method of treating inflammatory diseases, cognitive diseases, eye diseases, skin diseases and stress by administering therapeutically effective amount of present bioavailable turmeric composition to a subject in need thereof; wherein the therapeutically effective amount is 500 mg/per day.

The recommended dosage of present bioavailable composition given to a subject in need is 500 mg; wherein the subject is human or animal.

In another optional embodiment, the present bioavailable turmeric composition can also be prepared by using extract from fresh rhizomes/fresh plant parts such as ginger rhizome, Aloe vera leaf, vegetables such as potato, beet root, and fruits such as guava instead of fresh turmeric rhizome extract.

Various embodiments disclosed herein relate to a bioavailable and self-dispersible turmeric composition, comprising:

an extract of a fresh plant part selected from the group consisting of a ginger rhizome, Aloe vera leaf, a potato plant part, a beet root, and a guava fruit as a dispersing agent; and a dried turmeric rhizome extract containing 35% to 95% total curcuminoids by weight, wherein the extract of the fresh plant part and the dried turmeric rhizome extract are present in a ratio of between 0.5:50 v/w and 50:0.5 v/w.

Various embodiments disclosed herein relate to a process for preparation of a turmeric composition including an extract of a fresh plant part selected from the group consisting of a ginger rhizome, Aloe vera leaf, a potato plant part, a beet root, and a guava fruit as a dispersing agent. The process includes the steps of:

a) either:
   washing a fresh turmeric rhizome with water and slicing the washed rhizomes, followed by squeezing the sliced plant part to separate a liquid extract and filtering the liquid extract;
   slicing the plant part and washing the sliced plant part with water, followed by squeezing the sliced plant part to separate a liquid extract and filtering the liquid extract;
b) heating the liquid extract of step (a) to a temperature of up to 60° C. with stirring;
c) adding the dried turmeric rhizome extract containing 35% to 95% total curcuminoids by weight to the heated liquid extract of step (b) to form a mixture;
d) homogenizing the mixture of step (c) for 30 to 60 minutes between 25° C. and 60° C. at 1400 RPM to obtain a slurry; and
e) drying the slurry of step (d) to obtain flakes.

EXAMPLE

Some typical examples illustrating the embodiments of the present invention are provided; however, these examples are exemplary only and should not be regarded as limiting the elements of the present invention.

Example 1: Turmeric Composition 1

| Sr. No. | Ingredients | Quantity (g) |
|---|---|---|
| 1. | Turmeric rhizome extract powder (Standardized) | 90 |
| 2. | Fresh turmeric rhizome extract (on dry basis) | 10 |
|  | Total | 100 |

Example 2: Components in Turmeric Composition 1

| Sr. No. | Components | Quantity (%) |
|---|---|---|
| 1. | Curcuminoids content | 50 to 94% |
| 2. | Proteins content | 0.25 to <4% |
| 3. | Carbohydrates content | 0.25 to <49% |

Example 3: Process for Preparation of Turmeric Composition 1 a) Washing 2.82 kg of fresh turmeric rhizome with RO water, slicing the washed rhizome, followed by squeezing the sliced rhizome using low speed screw extruder with 0.5 mm to 1 mm mesh to separate the liquid extract and filtering the extract;

b) heating the extract obtained in step (a) up to 60° C. with continuous stirring for 30 minutes using a homogenizer;

c) adding 1.8 kg of dried turmeric rhizome extract (standardized to >55% total curcuminoids) slowly to the extract of step (b) with continuous homogenizing for 30 to 60 minutes at 1400 RPM between 25° C. to 60° C. to obtain viscous slurry;

d) vacuum drying the slurry of step (c) at 60° C. to 85° C., 650 mmHg vacuum for 8 hours using Rotary Vacuum Dryer (RVD); and e) milling the flakes of step (d) to obtain free flowing powder (particle size >120 mesh) of self-dispersible turmeric composition.

Yield of fresh extract: 1.8 kg

Example 4: Release Profile of Turmeric Composition 1

The composition was tested for solubility of curcuminoids and its release in buffer. 500 mg of Composition 1 of Example 1 (Test product) and unformulated standard curcuminoids [standardized to 95% Curcuminoids (C-95)] were added into the 400 ml phosphate buffer (pH 6.8) in separate beakers under stirring at 37° C. Samples were drawn for up to four hours, filtered/centrifuged and tested for curcumin content by measuring absorbance at 424 nm using UV-Vis spectrophotometer. The result shows the increased solubility and release profile of Composition 1 compared to unformulated standard curcuminoids [standardized to 95% Curcuminoids (C-95)] (Reference product). The absorbance vs. time graph was plotted as illustrated in FIG. 1.

Example 5: Curcuminoids Content of Turmeric Composition 1

The composition was tested for total Curcuminoids and the result is given below:

| Total Curcuminoids Assay by HPLC | |
|---|---|
| Curcumin | 30.46% |
| Desmethoxycurcumin | 12.54% |
| Bisdemethoxycurcumin | 9.70% |
| Total Curcuminoids | 52.70% |

Example 6: Comparative Self-Dispersion Profile of Turmeric Composition 1 Vis-à-vis Unformulated Standard Curcuminoids (95% Total Curcuminoids, C-95)

A comparative self-dispersion study was carried out between the Composition 1 (Test product) and unformulated Standard Curcuminoids having 95% total curcuminoids (Reference product, C-95). The dispersion is given in FIG. 2. The result shows that the test product showed enhanced self-dispersion compared to the reference product. There was no self-dispersion/dispersion observed for reference product

Example 7: Comparative Bioavailability Studies of the Turmeric Composition 1 Vis-à-vis Unformulated Standard Curcuminoids (95% Total Curcuminoids)

A comparative oral bioavailability study of Composition 1 (Test product) and unformulated Standard Curcuminoids (standardized to 95%) (Reference product) was carried out in healthy adult human subjects (n=18). Relative bioavailability and pharmacokinetics of total curcumin was evaluated following oral administration of single dose of test product equivalent to 2 g Curcuminoids Vs. unformulated standard Curcuminoids (standardized to 95%) equivalent to 2 g Curcuminoids. The blood samples were collected at 00.00, 00.25, 00.50, 01.00, 01.50, 02.00, 02.50, 03.00, 03.50, 04.00, 06.00, 08.00, 12.00, 16.00 and 24.00 hours post dose and were centrifuged at 3800 rpm for 10 minutes at 2° C. to 8° C. for separating the plasma. The plasma samples were treated with β-Glucuronidase/sulfatase (EC 3.2.1.31) from *Helix pomatia* in 0.1M phosphate for 1 hour at 37° C. to ensure the complete hydrolysis of glucuronide/sulfate conjugates of Curcuminoids. Then, the curcuminoids were extracted with 2 ml of extraction solvent [Ethyl Acetate:Acetonitrile (95:05)] and evaporated to dryness under the stream of nitrogen. The dried residue was reconstituted in 0.5 ml of mobile phase and analyzed for total curcumin, demethoxycurcumin (DMC) and bisdemethoxycurcumin (BDMC) and tetrahydrocurcumin (THC) using LC-MS/MS.

Total Curcuminoids (Curcumin, Demethoxycurcumin, and Bisdemethoxycurcumin) were quantified against respective USP standard. Curcumin-D6 was used as internal standard (ISTD). The mean total plasma Curcumin, Demethoxycurcumin, Bisdemethoxycurcumin and Tetrahydrocurcumin concentration vs. time graphs for 'Test product' and 'Reference product' was plotted as illustrated in FIGS. 3, 4, 5 and 6 respectively.

Pharmacokinetic Results: The pharmacokinetic result of Turmeric Composition 1 is given in below Table 1 to Table 4 as follows:

TABLE 1

Mean of Pharmacokinetic Parameters of Total Curcumin

| PK Parameter (Units) | Test product | Reference Product |
|---|---|---|
| $C_{max}$ (ng/mL) | 193.22 | 7.62 |
| $AUG_{0-t}$ (ng · hr/mL) | 1225.82 | 24.77 |
| $T_{max}$ (hr)* | 4.0 (3.50, 16.00) | 2.00 (0.50, 12.00) |

*For $T_{max}$, Median (Min, Max) are presented

TABLE 2

Mean of Pharmacokinetic Parameters of Demethoxycurcumin (DMC)

| PK Parameter (Units) | Test Product | Reference Product |
|---|---|---|
| $C_{max}$ (ng/mL) | 125.20 | 7.12 |
| $AUG_{0-t}$ (ng · hr/mL) | 856.94 | 19.68 |
| $T_{max}$ (hr)* | 4.00 (3.50, 16.00) | 1.50 (0.50, 3.50) |

*For $T_{max}$, Median (Min, Max) are presented

TABLE 3

Mean of Pharmacokinetic Parameters of Bisdemethoxycurcumin (DMC)

| PK Parameter (Units) | Test Product | Reference Product |
|---|---|---|
| $C_{max}$ (ng/mL) | 32.11 | 3.81 |
| $AUG_{0-t}$ (ng · hr/mL) | 256.95 | 5.49 |
| $T_{max}$ (hr)* | 3.00 (1.50, 8.00) | 1.50 (0.50, 3.50) |

*For $T_{max}$, (Min, Max) are presented

TABLE 4

Mean of Pharmacokinetic Parameters of Tetrahydrocurcumin (THC)

| PK Parameter (Units) | Test Product | Reference Product |
|---|---|---|
| $C_{max}$ (ng/mL) | 10.95 | 0.66 |
| $AUC_{0-t}$ (ng · hr/mL) | 44.17 | 1.427 |
| $T_{max}$ (hr)* | 3.00 (1.50, 6.00) | 1.50 (1.00, 3.00) |

*For $T_{max}$, Median (Min, Max) are presented
$C_{max}$: Maximum measured Plasma concentration
$AUC_{0-t}$: The area under the Plasma concentration versus time curve from time '0' to specified time
$T_{max}$: Time of the maximum measured plasma concentration (Minimum and Maximum median is presented).

The mean plasma Total Curcumin concentration Vs. time graph for 'Test product' and 'Reference product' is given in FIG. 3. The pharmacokinetic result is given in Table 1. The results from Table 1 showed that the $C_{max}$ and $AUC_0$-t of the test product for Total Curcumin was 25.35 times and 49.48 times higher than the $C_{max}$ and $AUC_{0-t}$ of the Reference product (unformulated Standard Curcuminoids) respectively.

The mean plasma Demethoxycurcumin (DMC) concentration Vs. time graph for 'Test product' and 'Reference product' is given in FIG. 4. The pharmacokinetic result is given in Table 2. The results from Table 2 showed that the $C_{max}$ and $AUC_{0-t}$ of the Test product for Demethoxycurcumin was 17.58 times and 43.53 times higher than the $C_{max}$ and $AUC_{0-t}$ of the Reference product (unformulated Standard Curcuminoids) respectively.

The mean plasma Bisdemethoxycurcumin (BDMC) concentration Vs. time graph for 'Test product' and 'Reference product' is given in FIG. 5. The pharmacokinetic result is given in Table 3. The results from Table 3 showed that the $C_{max}$ and $AUC_{0-t}$ of the test product for Bisdemethoxycurcumin was 8.41 times and 46.79 times higher than the $C_{max}$ and $AUC_{0-t}$ of the Reference product (unformulated Standard Curcuminoids) respectively.

The mean plasma Tetrahydrocurcumin (THC) concentration Vs. time for 'Test product' and 'Reference product' is given in FIG. 6. The pharmacokinetic result is given in Table 4. The results from Table 4 showed that the $C_{max}$ and $AUC_0$-t of the test product for Tetrahydrocurcumin was 16.71 times and 30.95 times higher than the $C_{max}$ and $AUC_{0-t}$ of the Reference product (unformulated Standard Curcuminoids) respectively.

It was concluded from above FIGS. 3 to 6 and Tables 1 to 4 that, the 'Test product' was found to be superior to 'Reference product' in enhancing the bioavailability of total Curcumin, Demethoxycurcumin (DMC), Bisdemethoxycurcumin (BDMC) and Tetrahydrocurcumin (THC). Plasma concentrations of DMC and BDMC were surprisingly found to be significantly higher.

Example 8: Turmeric Composition 2

| Sr. No. | Ingredients | Quantity (g) |
|---|---|---|
| 1. | Turmeric rhizome extract powder (Standardized) | 90 |
| 2. | Fresh turmeric rhizome extract (on dry basis) | 10 |
|  | Total | 100 |

Example 9: Process for Preparation of Turmeric Composition 2 a) Washing 150 gm of fresh turmeric rhizome with RO water, slicing the washed rhizome, followed by squeezing the sliced rhizome using low speed screw extruder with 0.5 mm to 1 mm mesh to separate liquid extract and filtering the extract;
b) heating the extract obtained in step (a) up to 60° C. with continuous stirring for 30 minutes using a homogenizer;
c) adding 90 g of dried turmeric rhizome extract (standardized to 60% total curcuminoids) slowly to the extract of step (b) with continuous homogenizing for 30 to 60 minutes at 1400 RPM between 25° C. to 60° C. to obtain viscous slurry;
d) vacuum drying the slurry of step (c) at 60° C. 85° C., 650 mmHg vacuum for 8 hours by Rotary Vacuum Dryer (RVD); and
e) milling the flakes of step (d) to obtain free flowing powder (particle size >120 mesh) of self-dispersible turmeric composition.

Yield of fresh extract: 100 g

Example 10: Release Profile of Turmeric Composition 2

The composition was tested for its active ingredient solubility and release in buffer. 500 mg of Composition 2 of Example 8 and unformulated standard curcuminoids [standardized to 95% Curcuminoids (C-95)] were added into the 400 ml phosphate buffer (pH 6.8) in separate beakers under intermittent stirring at 37° C. Samples were drawn for up to four hours, filtered/centrifuged and tested for curcumin content by measuring absorbance at 424 nm using UV-Vis spectrophotometer. The results shows the increased solubility and release profile for Composition 2 compared to standard curcumin extract [standardized to 95% Curcuminoids (C-95%)]. The absorbance vs. time graph was plotted as illustrated in FIG. 7.

Example 11: Curcuminoids Content of Turmeric Composition 2

The composition was tested for total Curcuminoids and the result is given below:

| Total Curcuminoids Assay by HPLC | |
|---|---|
| Curcumin | 30.68% |
| Desmethoxycurcumin | 12.60% |
| Bisdemethoxycurcumin | 9.74% |
| Total Curcuminoids | 53.02% |

Example 12: Turmeric Composition 3

| Sr. No. | Ingredients | Quantity (g) |
|---|---|---|
| 1. | Turmeric rhizome extract powder (Standardized) | 80 |
| 2. | Fresh turmeric rhizome extract (on dry basis) | 20 |
|  | Total | 100 |

Example 13: Process for Preparation of Turmeric Composition 3 a) Washing 250 g of fresh turmeric rhizome with RO water, slicing the washed rhizome, followed by squeezing the sliced rhizome using low screw extruder with 0.5 mm to 1 mm mesh to separate liquid extract and filtering the extract;
b) heating the extract obtained in step (a) up to 60° C. with continuous stirring for 30 minutes using a homogenizer;
c) adding 80 g of dried turmeric rhizome extract (standardized to 55% total curcuminoids) slowly to the extract of step (b) with continuous homogenizing for 30 to 60 minutes at 1400 RPM between 25° C. to 60° C. to obtain viscous slurry;
d) vacuum drying the slurry of step (c) at 60° C. 85° C., 650 mmHg vacuum for 8 hours by Rotary Vacuum Dryer (RVD); and
e) milling the flakes of step (d) to obtain free flowing powder (particle size >120 mesh) of self-dispersible turmeric composition Yield of fresh extract: 200 g

Example 14: Release Profile of Turmeric Composition 3

The composition was tested for its active ingredient solubility and release in buffer. 500 mg of Composition 3 of Example 12 and unformulated standard curcuminoids [standardized to 95% Curcuminoids (C-95)] were added into the 400 ml phosphate buffer (pH 6.8) under intermittent stirring at 37° C. Samples were drawn for up to five hours and tested for curcuminoid content by measuring absorbance at 424 nm using UV-Vis spectrophotometer. The result shows that Composition 3 has enhanced solubility and release profile compared to unformulated standard curcumin extract [standardized to 95% Curcuminoids (C-95%)]. The absorbance vs. time graph was plotted as illustrated in FIG. 8.

Example 15: Curcuminoids Content of Turmeric Composition 3

The composition was tested for total Curcuminoids and the result is given below:

| Total Curcuminoids Assay by HPLC | |
|---|---|
| Curcumin | 34.30% |
| Desmethoxycurcumin | 10.43% |
| Bisdemethoxycurcumin | 7.20% |
| Total Curcuminoids | 51.93% |

Example 16: Turmeric Composition 4

| Sr. No. | Ingredients | Quantity (g) |
|---|---|---|
| 1. | Turmeric rhizome extract powder (Standardized) | 70 |
| 2. | Fresh turmeric rhizome extract (on dry basis) | 30 |
| | Total | 100 |

Example 17: Process for Preparation of Turmeric Composition 4 a) Washing 400 g of fresh turmeric rhizome with RO water, slicing the washed rhizome, followed by squeezing the sliced rhizome using low screw extruder with 0.5 mm to 1 mm mesh to separate liquid extract and filtering the extract;
b) heating the extract obtained in step (a) up to 60° C. with continuous stirring for 30 minutes using a homogenizer;
c) slowly adding 70 g of dried turmeric rhizome extract (standardized to 95% total curcuminoids) to the extract of step (b) with continuous homogenizing for 30 to 60 minutes at 1400 RPM between 25° C. to 60° C. to get viscous slurry;
d) vacuum drying the slurry of step (c) at 60° C. 85° C., 650 mmHg vacuum for 8 hours by Rotary Vacuum Dryer (RVD); and
e) milling the flakes of step (d) to obtain free flowing powder (particle size >120 mesh) of self-dispersible turmeric composition.

Yield of fresh extract: 300 g

Example 18: Release Profile of Turmeric Composition 4

The composition was tested for its active ingredient solubility and release in buffer. 500 mg of Composition 4 of Example 16 and unformulated standard curcuminoids [standardized to 95% Curcuminoids (C-95)] were added into 400 ml phosphate buffer (pH 6.8) under intermittent stirring at 37° C. Samples were drawn for up to four hours and tested for curcuminoid content by measuring absorbance at 424 nm using UV-Vis spectrophotometer. The result shows that Composition 4 has enhanced solubility and release profile compared to standard curcumin extract [standardized to 95% Curcuminoids (C-95)]. The absorbance vs. time graph was plotted as illustrated in FIG. 9.

Example 19: Curcuminoids Content of Turmeric Composition 4

The composition was tested for total curcuminoids and the result is given below:

| Total Curcuminoids Assay by HPLC | |
|---|---|
| Curcumin | 53.93% |
| Demethoxycurcumin | 12.17% |
| Bisdemethoxycurcumin | 2.26% |
| Total Curcuminoids | 68.36% |

Example 20: Turmeric Composition 5

| Sr. No. | Ingredients | Quantity (g) |
|---|---|---|
| 1. | Turmeric rhizome extract powder (Standardized) | 85 |
| 2. | Fresh turmeric rhizome extract (on dry basis) | 15 |
| | Total | 100 |

Example 21: Process for Preparation of Turmeric Composition 5 a) Washing 200 g of fresh turmeric rhizome with RO water, slicing the washed rhizome, followed by squeezing the sliced rhizome using low screw extruder with 0.5 mm to 1 mm mesh to separate liquid extract and filtering the extract;
b) heating the extract obtained in step (a) up to 60° C. with continuous stirring for 30 minutes using a homogenizer;
c) slowly adding 85 g of dried turmeric rhizome extract (standardized to 95% total curcuminoids) to the extract of step (b) with continuous homogenizing for 30 to 60 minutes at 1400 RPM between 25° C. to 60° C. to get viscous slurry;
d) vacuum drying the slurry of step (c) at 60° C. 85° C., 650 mmHg vacuum for 8 hours by Rotary Vacuum Dryer (RVD); and
e) milling the flakes of step (d) to obtain free flowing powder (particle size >120 mesh) of self-dispersible turmeric composition.

Yield of fresh extract: 150 g

Example 22: Release Profile of Turmeric Composition 5

The composition was tested for its active ingredient solubility and release in buffer. 500 mg of Composition 5 of Example 20 and unformulated standard curcuminoids [standardized to 95% Curcuminoids (C-95)] were added into the 400 ml phosphate buffer (pH 6.8) under intermittent stirring at 37° C. Samples were drawn for up to four hours and tested for curcuminoid content by measuring absorbance at 424 nm using UV-Vis spectrophotometer. The result shows that the Composition 5 has enhanced solubility and release profile compared to unformulated standard curcumin extract [standardized to 95% Curcuminoids (C95)]. Absorbance vs. time graph was plotted as illustrated in FIG. 10.

Example 23: Curcuminoids Content of Turmeric Composition 5

The composition was tested for total Curcuminoids and the result is given below:

| Total Curcuminoids Assay by HPLC | |
|---|---|
| Curcumin | 62.99% |
| Demethoxycurcumin | 14.03% |
| Bisdemethoxycurcumin | 2.40% |
| Total Curcuminoids | 79.42% |

Example 24: Release Profile of Turmeric Composition 1 of Example 1 Vis-à-vis Standard Curcumin Extract (95% Total Curcuminoids) and Fresh Turmeric Rhizome Extract The composition was tested for its active ingredient solubility and release in buffer. 500 mg of Composition 1 of Example 1 (Test product), unformulated standard curcuminoids [standardized to 95% Curcuminoids (C-95)] and fresh turmeric rhizome extract were added into the 400 ml phosphate buffer (pH 6.8) in separate beakers under intermittent stirring at 37° C. Samples were drawn for up to five hours, filtered/centrifuged and tested for curcumin content by measuring absorbance at 424 nm using UV-Vis spectrophotometer. The result shows the increased release profile for 'Test product' compared to 'unformulated standard curcumin extract (95% total curcuminoids)' and 'fresh turmeric rhizome extract'. Absorbance vs. time graph was plotted as illustrated in FIG. 11.

Example 25: Release Profile of Turmeric Composition 1 of Example 1 vs. Marketed Product The composition was tested for its active ingredient solubility and release in buffer. 500 mg of Composition 1 of Example 1 (Test product) and marketed product were added into the 400 ml phosphate buffer (pH 6.8) in separate beakers under intermittent stirring at 37° C. Samples were drawn for up to five hours, filtered/centrifuged and tested for curcumin content by measuring absorbance at 424 nm using UV-Vis spectrophotometer. The result shows the increased release profile for 'Test product' compared to the 'marketed product'. The Absorbance vs. time graph was plotted as illustrated in FIG. 12.

Example 26: Turmeric Composition 6

| Sr. No. | Ingredients | Quantity (g) |
| --- | --- | --- |
| 1. | Turmeric rhizome extract powder (Standardized to 56% total curcuminoids) | 94 |
| 2. | Fresh turmeric rhizome extract (on dry basis) | 6 |
|  | Total | 100 |

Example 27: Curcuminoids Content of Turmeric Composition 6

The composition of Example 26 was tested for total Curcuminoids and the result is given below:

| Total Curcuminoids Assay by HPLC | |
| --- | --- |
| Curcumin | 32.10% |
| Demethoxycurcumin | 12.54% |
| Bisdemethoxycurcumin | 9.78% |
| Total Curcuminoids | 54.42% |

We claim:

1. A bioavailable and self-dispersible turmeric composition, comprising:
   10% to 30% by weight of a powdered juice extract of fresh turmeric rhizomes comprising <4% hydrophobic contents by weight as a dispersing agent; and
   70% to 90% by weight of a dried oleoresin extract of a turmeric rhizome containing 35% to 95% total curcuminoids by weight,
   wherein the powdered juice extract of fresh turmeric rhizomes comprises <2% curcuminoids; and the turmeric composition contains 0.25% to <4% of proteins by weight.

2. The turmeric composition as claimed in claim 1, wherein the extract of fresh turmeric rhizomes is obtained from turmeric rhizomes containing >60% water by weight.

3. The turmeric composition as claimed in claim 1, wherein the extract of fresh turmeric rhizomes contains <2% curcuminoids.

4. The turmeric composition as claimed in claim 1, wherein the turmeric composition is free of externally added excipients, bio-enhancing agents, emulsifiers, dispersing agents, solvents, fixed oils, volatile oils, and gums.

5. The turmeric composition as claimed in claim 1, wherein the turmeric composition comprises:
   20% to 85% by weight of total curcuminoids in a self-dispersible form; and
   0.25% to <49% of carbohydrates.

6. The turmeric composition as claimed in claim 1, wherein:
   the turmeric composition comprises 20% to 85% by weight of total curcuminoids in a self-dispersible form, and
   the total curcuminoids comprise:
      curcumin in an amount of 15% to 74%,
      desmethoxycurcumin (DMC) in an amount of 10% to 30%, and
      bisdemethoxycurcumin (BDMC) in an amount of 3% to 20%.

7. The turmeric composition as claimed in claim 1, wherein the turmeric composition is in the form of a powder, and is formulated into a dosage form selected from the group consisting of tablets, capsules, pills, solutions, pastes, lozenges, ready to drink beverages (RTD), beverages, fortified food, chocolates and combinations thereof.

8. The turmeric composition as claimed in claim 1, wherein the turmeric composition is configured to deliver higher levels of curcumin, desmethoxycurcumin (DMC), bisdemethoxycurcumin (BDMC) and tetrahydrocurcumin (THC) into the blood of a subject than a comparative standard curcumin extract due to the powdered juice extract dispersing agent, wherein:
   the turmeric composition comprises 52% to 80% curcuminoids; and
   the comparative curcumin extract comprises 95% curcuminoids.

9. A bioavailable and self-dispersible turmeric composition, comprising:
   a turmeric formulation, comprising:
      5% to 80% by weight of a solvent free powdered juice extract of fresh turmeric rhizomes comprising <2% curcuminoids by dry weight,
      20% to 95% by weight of a dried turmeric rhizome extract containing 35% to 95% total curcuminoids by weight, and
      0.25% to <4% of proteins,
      based on the combined weight of the powdered juice extract and the dried turmeric rhizome extract,
   wherein the turmeric formulation is present in an amount effective to treat an inflammatory disease, a cognitive disease, an eye disease, a skin disease, stress, or a combination thereof.

10. The turmeric composition as claimed in claim 9, wherein the turmeric formulation comprises:
- 5% to 30% by weight of the solvent free powdered juice extract of fresh turmeric rhizomes, and
- 70% to 95% by weight of the dried turmeric rhizome extract,
- based on the combined weight of the powdered juice extract and the dried turmeric rhizome extract.

11. The turmeric composition as claimed in claim 9, wherein the turmeric composition is free of externally added excipients, bio-enhancing agents, emulsifiers, dispersing agents, solvents, fixed oils, volatile oils, and gums.

12. The turmeric composition as claimed in claim 9, wherein the turmeric composition comprises:
- 20% to 85% by weight of total curcuminoids in a self-dispersible form,
- 0.25% to <4% of proteins; and
- 0.25% to <49% of carbohydrates.

13. The turmeric composition as claimed in claim 9, wherein:
- the turmeric composition comprises 20% to 85% by weight of total curcuminoids in a self-dispersible form, and
- the total curcuminoids comprise:
    - curcumin in an amount of 15% to 74%,
    - desmethoxycurcumin (DMC) in an amount of 10% to 30%, and
    - bisdemethoxycurcumin (BDMC) in an amount of 3% to 20%.

* * * * *